(12) United States Patent
Brockhoff et al.

(10) Patent No.: US 6,478,962 B1
(45) Date of Patent: Nov. 12, 2002

(54) DYNAMIC BUBBLE TRAP

(76) Inventors: Alexander Brockhoff, Gebhardstorkel 10, FL-9494 Schaan, Furstentum (LI); Hans Plechinger, Cherry Creek Ranch SS 3 Site 15-130, Cranbrook, B.C. (CA); Hans-Jurgen Tiedke, Lochner Str. 30, Aachen, 52064 (DE)

( * ) Notice: Subject to any disclaimer, the term of this patent is extended or adjusted under 35 U.S.C. 154(b) by 0 days.

(21) Appl. No.: 09/545,637

(22) Filed: Apr. 7, 2000

Related U.S. Application Data

(63) Continuation-in-part of application No. 08/998,500, filed on Dec. 26, 1997, now abandoned, which is a continuation of application No. 08/571,490, filed on Dec. 13, 1995, now Pat. No. 5,824,212.
(60) Provisional application No. 60/128,346, filed on Apr. 8, 1999.

(51) Int. Cl.[7] .............................. B04C 3/00; B04C 3/06; B61D 19/00
(52) U.S. Cl. .................... 210/512.1; 210/188; 210/194; 209/715; 209/717; 209/725; 209/734; 96/155; 96/204; 96/206; 96/208; 55/338; 55/447; 55/459.3; 55/461

(58) Field of Search ................................ 210/781, 782, 210/787, 788, 188, 194, 512.1; 55/459.1, 459.3, 338, 447, 461; 96/204, 155, 206, 208; 604/4.01; 95/261, 269

(56) References Cited

U.S. PATENT DOCUMENTS 5,965,021 A * 10/1999 Hesse et al. ............. 210/512.1

FOREIGN PATENT DOCUMENTS

| GB | 1526509 | * | 9/1978 |
| GB | 2 063 108 A | * | 6/1981 |

* cited by examiner

Primary Examiner—David A. Reifsnyder
(74) Attorney, Agent, or Firm—Beck & Tysver P.L.L.C.

(57) ABSTRACT

The bubble trap is used in extracorporeal blood flow circuits of the type used for open heart surgery. The trap is placed in the external blood flow and it removes small micro bubbles from the blood prior to delivery to the body. The device accelerates the blood flow radially and the small bubbles migrate toward the center of the accelerated flow. These bubbles are concentrated at this location and the blood that contains the micro bubbles is extracted and recirculated before the degassed blood flow is returned to the body.

8 Claims, 2 Drawing Sheets

DYNAMIC BUBBLE TRAP

CROSS REFERENCE TO RELATED APPLICATION

This application Ser. No. 09/545,637 is a continuation-in-part of U.S. patent application No. 08/998,500, filed on Dec. 26, 1997, now abandoned, which is a continuation of U.S. patent application No. 08/571,490, filed on Dec. 13, 1995 which has Issued as U.S. Pat. No. 5,824,212.

This application claims the benefit of Provisional Application No. 60/128,346, filed on Apr. 8, 1999.

FIELD OF THE INVENTION

The present invention relates generally to "bubble trap" devices that are used for removing gas bubbles from the extracorporeal circulation of blood.

BACKGROUND OF THE INVENTION

Open heart surgery as well as other modern surgical procedures require that the patient's blood be routed to an extracorporeal blood pump and oxygenator system. Extracorporeal support of blood perfusion provides many opportunities form air to be mixed with the circulating blood. Consequently it has become conventional practice to place a fine mesh filter called a "bubble trap" close to the blood return cannula. This device serves to trap gas bubbles before they are introduced into the body. This is an essential safety precaution as it is well known that gas bubbles can cause embolisms to form in the vasculature. Since the typical aortic return cannula commonly used in open heart surgery is located near the vessels that communicate with the brain, the possibility of a stroke from small bubbles is a distinct clinical concern. Recent evidence suggests that the presence of even very small micro bubbles is undesirable in perfusion procedures.

Bubbles having a diameter of just a few micrometers are impossible to remove using conventional filter technology. A porous mesh filter sufficiently small to "trap" a small bubble has a very high flow resistance and this results in a very high-pressure differential across the mesh which is undesirable. For this reason among others there is a continuing need to improve bubble trap technology.

SUMMARY OF THE INVENTION

The bubble trap of the present invention is inserted into the external "blood loop" and blood is forced through the dynamic bubble trap by the blood pump. Typically the device is placed just ahead of the outlet cannula to act as a final-filter for the removal of bubbles just prior to the delivery of blood to the patient. The bubble trap device splits the blood flow into two streams. The first stream is fully bubble free and it is delivered to the patient. The secondary stream is smaller and it contains the micro bubbles removed from the in coming blood flow. This secondary flow is returned to the extracorporeal circuit upstream of the trap for additional degassing.

The blood flows through the bubble trap device from end to end and thus this flow is primarily axial in direction. Within the bubble trap device the blood flow is subjected to a strong radial acceleration so that there is a strong radial velocity imparted to the blood flow as well. A specialized helical separation chamber is used to impart this radial acceleration. The helix within the separation section comprises a center body and one or more blades. The design and the cross sectional areas of the separation zone are optimized to treat the blood cells gently while applying enough force to the small bubbles to concentrate them for removal.

BRIEF DESCRIPTION OF THE DRAWINGS

Throughout the various figures like reference numerals represent identical or equivalent structures, wherein.

DETAILED DESCRIPTION

Throughout the description the dynamic bubble trap is described as a stand alone device placed in an extracorporeal blood circulation path for ease of explanation. However, it should be understood that the bubble trap device technology can be incorporated into other blood handling devices without departing from the scope of the invention. The preferred structures shown in the figures are illustrative and variations in the design can be carried out within the scope of the invention.

Figure 1:
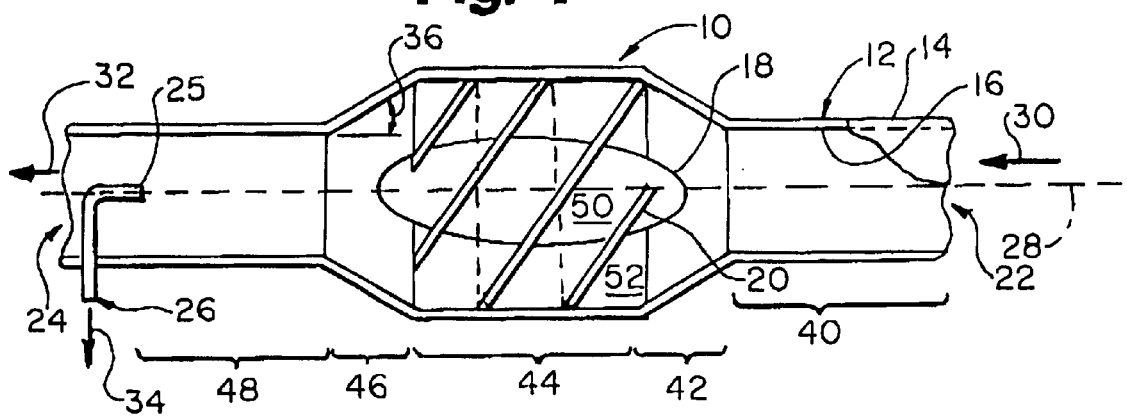
FIG. 1 is a schematic diagram showing a cross section of a dynamic bubble trap device.

Fig. 1 is a schematic drawing which shows the dynamic bubble trap 10 in partial cross section. The device includes a body 12 that has an exterior wall 14 and an interior wall 16. The overall shape of the device is elongate and approximately cylindrical, The blood flow through the device is primarily axial along the axis 28 of the body 12. A helix is placed inside the device 10 and this helical section is formed by a center body 18 coupled to a blade 20. In the figure, portions of the blade are shown in phantom dotted lines to clarify the figure. The blade 20 extends between the interior wall 16 and the surface of the center body 18. Various construction techniques can be used to realize the device 10. It has proved convenient to form the center body 18 and blade 20 as a unitary structure and to segment the body 12 to receive the helical section as an insert. Various other assembly techniques can be used as well.

As seen in FIG. 1 the device 10 includes a primary blood flow inlet 22 to receive blood flow 30 which contains micro bubbles. The device 10 also has a primary blood flow outlet 24 formed in the body for delivering bubble free blood flow 32. A secondary blood flow outlet 26 is also provided for the recirculation of secondary blood flow 34 which contains micro bubbles.

In operation, the primary inlet 22 and the primary outlet 24 are connected in an extracorporeal blood flow loop at or near the discharge or blood return cannula. The secondary recirculation from secondary blood flow outlet 26 is connected by the user to a location that returns this blood stream to the extracorporal flow system "upstream" of the bubble trap device 10. This allows the micro bubbles to be dissipated and this portion of blood to be further degassed in the system.

During operation the bubble trap device 10 divides the inlet blood flow 30, into a bubble free primary outlet blood flow 32 and a secondary blood flow 34 for recirculation. The device 10 is powered by the pressure gradient imparted to the primary blood flow 30 by the extracorporeal blood pump.

For the purposes of describing flow regimes within the device 10 the device maybe considered to have a supply section 40; an inlet section 42; a radial acceleration section 44; an outlet section 46 ands a separation section 48.

The inlet blood flow 30 is introduced into the device 10 at through the supply section 40. In this section 40 the blood flows smoothly in the axial direction defined by the axis 28. Next the blood flows from the supply section 40 to the inlet section 42 where the cross section of the device may change. As seen in the figure this area may be reduced to gently accelerate the flow along the axial direction and introduce the blood flow into the helical blades in the radial acceleration section 44.

In FIG. 1 blade 20 cooperates with the exterior wall 14 and the center body 18 to form two helical channels which imparts a rotary motion to the blood flow with respect to the axis 28. The blade 20 divides the flow path into two channels shown as blood flow channel 50 and blood flow channel 52. the two channels are parallel and both channels are defined by the blade 20. Although only one blade is shown in the figure for simplicity of illustration, more than one blade can be used. If multiple blades are used then there will be additional flow channels in the device 10.

In FIG. 1 the drawing shows the contour of the center body 18 as a "teardrop" shape which smoothly changes in diameter along the axis 28. The shape of this center body 50 defines the cross section of the flow path within the radial acceleration section 44. Alternate center body contours arc operable and shown in other figures.

The center body 18 seen in FIG. 1 is axially and radially symmetric and it is shown forming a gently converging channel to minimize disruption to the blood cells as they are radially accelerated in channels 50 and 52 defined by the stationary blade 20. The blade 20 seen in all the figure exhibits constant pitch however the pitch of the blade may be constant or the pitch may vary along the direction of flow. In the figures a single blade and a constant pitch configuration is shown for clarity and simplicity of description. The detail design of this portion of the device results in acceleration of the blood while minimize damage to the blood and it may be useful to vary both center body contour and blade number and pitch to achieve this result.

Immediately after the annular acceleration section 44 the blood flows into the outlet section 46 which functions in the exemplary embodiment as a diverging nozzle to slow the axial velocity of the blood passing through the device. In general the design of this section is compromised in favor of minimizing the pressure change on the blood cells. For this reason the included angle 36 defining the taper of this section may vary from about 5 degrees to about 45 degrees. The outlet section 46 cooperates with the separation section 48 to separate the micro bubbles from the blood flow. The blood removed through the secondary outlet 26 contains the concentrated flow of micro bubbles that have migrated toward the centerline of the flow along axis 28 under the force imparted by the radial acceleration section.

The shape of the inlet or bubble pick up 25 of the secondary blood flow outlet 26 may take any suitable form but round or circular opening s have proven effective.

Figure 2:
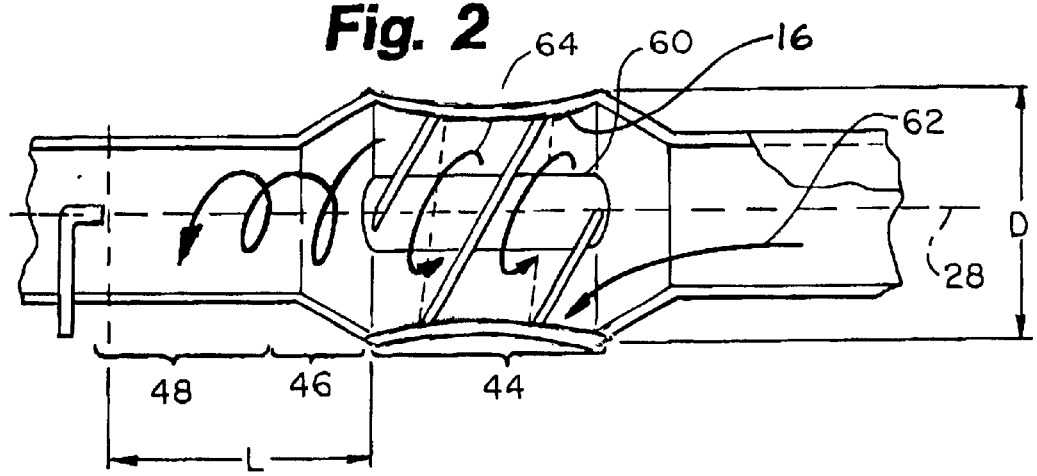
FIG. 2 is a schematic diagram showing a cross section of a dynamic bubble trap device.

FIG. 2 shows a schematic partial cross section of the bubble trap device 10 with an alternate form of center body 60. In this example the center body 60 is essentially cylindrical in form and has blunt entry surfaces. The interior wall 16 is concave to cooperate with the cylindrical body to accelerate the flow. In general the blood flow channel is defined by the space between the interior wall 16 and the center body 18 and either surface or both may vary in shape and contour. The dimension D may be taken as an average or characteristic dimension for the size of the helical flow section.

In this figure the blood flow is shown by flow stream line 62 which is shown entering the radial acceleration section 44. The blood spirals around the radial acceleration section 44 as depicted by flow streamline 64 which is intended to depict rotary motion about the axis 28. The blood exits the radial acceleration section 44 and continues to spiral around the axis 28 during transit through the outlet section 46 and the separation section 48.

It is believed that a substantial amount of time is require to allow the small micro bubbles (8 micron diameter) to migrate under the accelerations imparted by the radial acceleration section 44. It has been determined that the length of the separation section has an important impact on the efficiency of the device. It has been found empirically and supported by a mathematical model, that the relationships between the flow rate, diameters and lengths can result in optimum separation with minimum recirculation flow rate from the secondary outlet 26. These relationships are counterintuitive and can be expressed as ratios of certain geometric relationships. In general the length "L" of the combined separation section 46 and outlet section 48 should be at least 3 times as long as the diameter "D" of the annular acceleration section 44. In general the length of the combined separation section 48 and outlet section 463 be not more than 10 times as long as the diameter "D" of the annular acceleration section 44. It must be understood that these are estimates and that operation outside of these ranges is possible but less practical and efficient.

The nominal flow rate through the bubble trap is approximately 2–7 liters a minute for an adult and the nominal diameter "D" of the device is between 1 and 4 centimeters. The width of the channel in the screw section 46 depends on the detail design and some experimentation should be expected to minimize damage to the blood while imparting high radial accelerations. It must be remembered that the pitch of this section also controls the path length for the blood.

Figure 3:
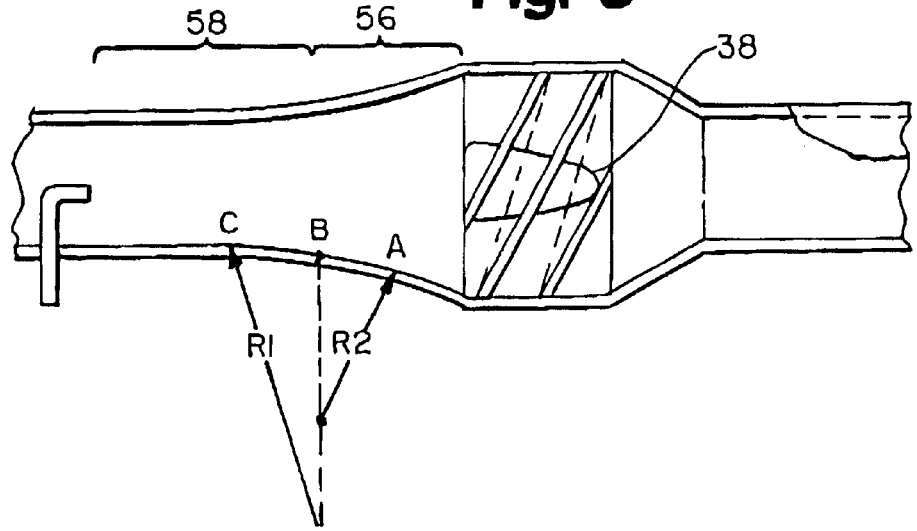
FIG. 3 is a schematic diagram showing a cross section of a dynamic bubble trap device; and, FIG. 4 is a schematic diagram showing a cross section of a dynamic bubble trap device.

FIG. 3 shows an alternate embodiment of the invention. In this embodiment the outlet section 56 and separation section 58 have rounded contours that may be expressed as radii. Although the actual shape may be quite complex the curve may be approximated by a circle of radius "R1" between points "A" and "B" and a second radius "R2 between points "B" and "C". In this embodiment the outlet section 56 blends smoothly with the separation section 58. The center body 38 is blunt on its leading edge and truncated on its trailing edge. Although this shape is not preferred it is associated with effective extraction and concentration of micro bubbles.

Figure 4:
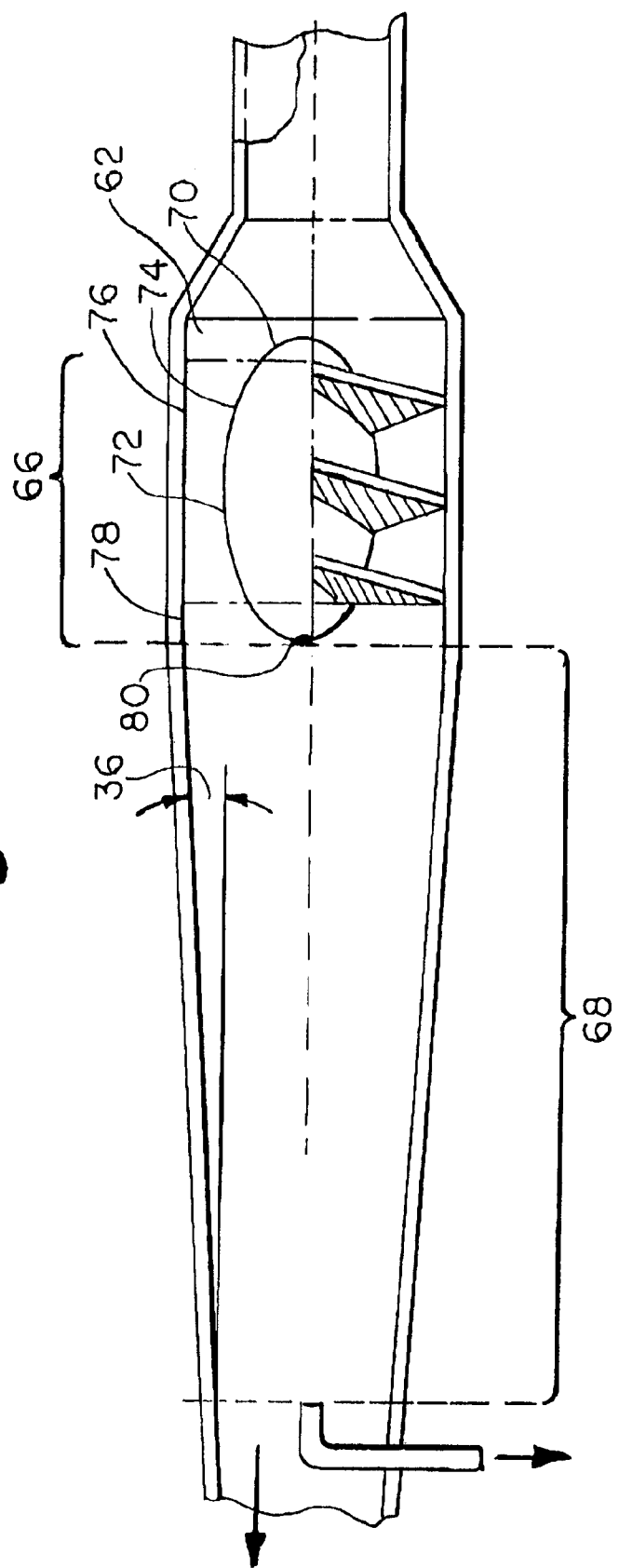

FIG. 4 shows a preferred design with the overall length of the combined outlet section and separation section 68 is more than 3 diameters away from the radial acceleration section 66. No distinct outlet section is apparent in this design. The included angle 36 defining the "straight" taper of the separation section is larger than 5 degrees. In this embodiment the center body 70 is shown in partial cut away to reveal the contour more clearly. In this instance the center body 70 is blunt at both ends and has a slightly steeper section after the maximum diameter station along the center body. The reference numeral 72 shows the maximum diameter station and this location is more than half way along the length of the radial acceleration section 66. In this fashion the center body is "sharper" at the leading edge of the flow in the radial acceleration section 66 than at the trailing edge of the radial acceleration section.

It is difficult to measure the operating pressures inside the radial acceleration section 66, however computation suggest that the maximum pressure gradient is achieved at a location approximately 25% of the total length of the radial acceleration section 66. This position is measured along the axis 28 and is depicted in the figure by reference numeral 74. The value of the pressures at this position are approximately –30 mm Hg at the surface of the center body shown at location 74 and a value of +5 mm Hg at the periphery of the flow next to the interior wall of the radial acceleration section indicated in the figure by reference numeral 76. As the flow moves along the radial acceleration section, the pressures change smoothly. The computed pressure at the exit of the radial acceleration section at the periphery at location 78 is near 0.0 mm Hg and the pressure at the end of the center body at location 80 is approximately −20 mmHg. These computed figures correspond to a geometry of an efficient and successful bubble trap. It is intended that variations from these computed and expected values are within the scope of the invention.

What is claimed is:

1. A device for removing bubbles from blood comprising:
   an elongate bubble trap body having an interior wall and exterior wall;
   said body having a longitudinal axis;
   a primary blood inlet and a primary blood outlet;
   a radial acceleration section located between said inlet port and said outlet;
   said radial acceleration section having;
      a blade coupled to a center body extending between said center body and said interior wall, forming at least one helical channel connecting said primary blood inlet to said primary blood outlet, for receiving blood from said inlet and to impart rotary motion to the blood flow, said blade making at least one revolution of said center body;
   said acceleration section having a nominal diameter D characteristic; said primary outlet located downstream of said acceleration section and said primary outlet having a single substantially circular outlet cross section centered on said longitudinal axis;
   a separation section located between said acceleration section and said primary outlet, said separation section and said primary outlet forming an outlet cone;
   a secondary blood outlet having a circular cross section, said circular cross section extending for a substantial distance along the length of said secondary outlet in the direction of blood flow downstream from said acceleration section;
   said secondary outlet positioned a distance L from said acceleration section and being upstream of said primary outlet where L is at least three times D the outer diameter of the acceleration section.

2. A device for removing bubbles from blood during extracorporeal transport according to claim 1, wherein the outlet cone converges linearly.

3. A device for removing bubbles from blood during extracorporeal transport according to claim 1, wherein the outlet cone converges smoothly.

4. A device for removing bubbles from blood comprising:
   an elongate bubble trap body having an interior wall and exterior wall;
   said body having a longitudinal axis;
   a primary blood inlet and a primary blood outlet;
   a radial acceleration section located between said inlet port and said outlet:
   said radial acceleration section having;
      at least one blade coupled to a center body extending between said center body and said interior wall, forming at least one helical channel connecting said primary blood inlet to said primary blood: outlet, for receiving blood from said inlet and to impart rotary motion to the blood flow, said helical channel making at least one revolution of said center body;
   said acceleration section having a nominal outer diameter D;
   said primary outlet having a single circular cross section located downstream of said acceleration section;
   a separation section located between said acceleration section and said primary outlet;
   a secondary blood outlet located a distance length L in the direction of blood flow downstream from said [separation] acceleration section;
   said secondary outlet positioned a distance L from said acceleration section and being upstream of said primary outlet where L is less than ten times D, the outer diameter of the acceleration section.

5. A device for removing bubbles from blood comprising:
   an elongate bubble trap body having an interior wall and exterior wall; said body having a longitudinal axis;
   a primary blood inlet and a primary blood outlet;
   a radial acceleration section located between said inlet port and said outlet:
   said radial acceleration section having;
      a blade coupled to a center body extending between said center body and said interior wall, forming at least one helical channel connecting said primary blood inlet to said primary blood outlet, for receiving blood from said inlet and to impart rotary motion to the blood flow, said blade making at least one revolution of said center body;
   said acceleration section having a nominal outer diameter D;
   said primary outlet having a single circular cross section with a center located on said longitudinal axis, located downstream of said acceleration section;
   a separation section located between said acceleration section and said primary outlet;
   a secondary blood outlet located a distance length L in the direction of blood flow downstream from said separation section;
   said secondary outlet positioned a distance L from said separation section and being upstream of said primary outlet where L is at least three times D but less than ten times D where D is the outer diameter of the acceleration section.

6. A device for removing bubbles from blood during extracorporeal transport, comprising:
   an elongate body having a primary blood inlet and a primary blood outlet, and a secondary blood outlet, aligned along a body axis;
   a separation section located between said primary inlet and said primary outlet, said separation section having:
      a helically shaped annular acceleration section to impart rotary motion on the blood flow, said acceleration section having an outer diameter D and said secondary blood outlet located a distance L which is between three and ten times the diameter D away from said acceleration section;
   said primary outlet having a varying circular diameter along the of flow direction thus defining an outlet cone, said outlet cone converging in the direction of blood flow and having a taper of between about 5 degrees and about 45 degrees measured to said body axis.

7. A device for removing bubbles from blood during extracorporeal transport according to claim 6, wherein the outlet cone converges linearly.

8. A device for removing bubbles from blood during extracorporeal transport according to claim 6, wherein the outlet cone converges smoothly.

* * * * *